(12) United States Patent
Kuhr et al.

(10) Patent No.: US 6,783,537 B1
(45) Date of Patent: Aug. 31, 2004

(54) LANCET DISPENSER

(75) Inventors: Hans-Juergen Kuhr, Mannheim (DE); Hans Kintzig, Tiefenthal (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/389,428

(22) Filed: Sep. 3, 1999

(30) Foreign Application Priority Data

Sep. 7, 1998 (DE) .......................................... 198 40 856

(51) Int. Cl.[7] ............................................. A61B 17/14
(52) U.S. Cl. ..................................... 606/182; 206/438
(58) Field of Search .................... 606/181–186, 606/167, 217–219; 227/176.1, 180.1, 181.1, 178.1, 175.1; 206/355, 356, 366, 370, 380, 381, 438, 354, 359, 349, 365, 377, 382, 363, 439, 364, 352; D8/70; D24/145; 221/113

(56) References Cited

U.S. PATENT DOCUMENTS

| | | | | |
|---|---|---|---|---|
| 3,030,959 A | | 4/1962 | Grunert ........................ 128/329 |
| 3,244,317 A | * | 4/1966 | Raybin .......................... 221/41 |
| 3,696,915 A | * | 10/1972 | Douglas ........................ 206/16 |
| 3,833,146 A | * | 9/1974 | Braginetz ..................... 221/66 |
| 4,442,836 A | | 4/1984 | Meinecke et al. ........... 128/314 |
| 4,794,926 A | | 1/1989 | Munsch et al. .............. 128/314 |
| 4,821,878 A | * | 4/1989 | Jones ............................ 206/370 |
| 4,860,937 A | * | 8/1989 | Arnold ......................... 227/147 |
| 4,998,452 A | * | 3/1991 | Blum ............................ 81/57.37 |
| 5,035,704 A | | 7/1991 | Lambert et al. ............. 606/182 |
| 5,152,775 A | | 10/1992 | Ruppert ........................ 606/182 |
| 5,318,584 A | | 6/1994 | Lange et al. ................. 606/182 |
| 5,478,345 A | * | 12/1995 | Stone et al. .................. 606/144 |
| 5,514,152 A | | 5/1996 | Smith ........................... 606/182 |
| 5,531,763 A | * | 7/1996 | Mastri et al. ................. 606/148 |
| 5,554,166 A | | 9/1996 | Lange et al. ................. 606/182 |
| 5,632,410 A | * | 5/1997 | Moulton et al. .............. 221/79 |
| 5,662,669 A | * | 9/1997 | Abidin et al. ................. 606/167 |
| 5,829,589 A | * | 11/1998 | Nguyen et al. .............. 206/366 |
| 6,472,220 B1 | * | 10/2002 | Simons et al. ................ 436/63 |

FOREIGN PATENT DOCUMENTS

| | | | |
|---|---|---|---|
| DE | 28 03 345 B1 | 6/1979 | ............ A61B/5/14 |
| EP | 0565970 A1 | 10/1993 | ............ A61B/5/14 |
| WO | WO98/14125 | 4/1998 | ........... A61B/17/32 |

* cited by examiner

Primary Examiner—Lien Tm Ngo
(74) Attorney, Agent, or Firm—Bose McKinney & Evans LLP

(57) ABSTRACT

A system suitable for collecting a body fluid, in particular blood from a body region of a person to be examined which comprises a lancing device which is suitable for holding a lancet, a lancet magazine for storing two or several lancets which has a transport device for the lancets and has an opening into which the lancing device can be inserted to remove a lancet from the lancet magazine, and two or several lancets, and which comprises a method for removing a lancet from a lancet magazine in which a lancet located in the lancet magazine is manually or automatically transported into a removal position in the interior of the lancet magazine, a lancing device is partially inserted into the opening provided in the lancet magazine in the process of which the lancing device automatically grips the lancet located in the removal position when it is partially inserted and the lancing device with the gripped lancet is removed from the lancet magazine.

6 Claims, 6 Drawing Sheets

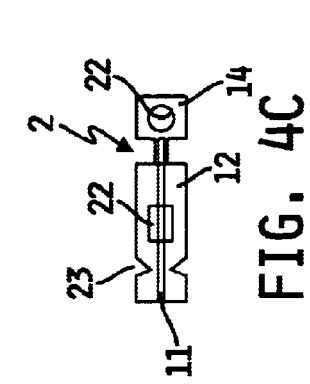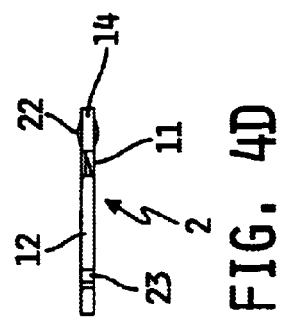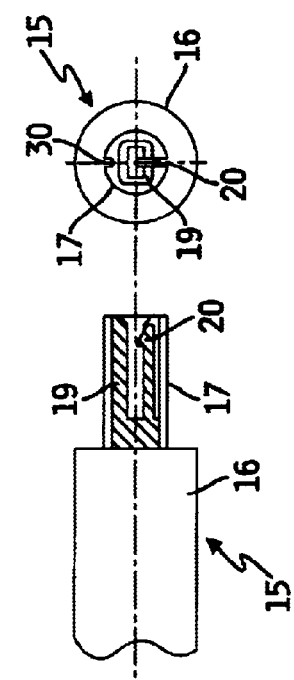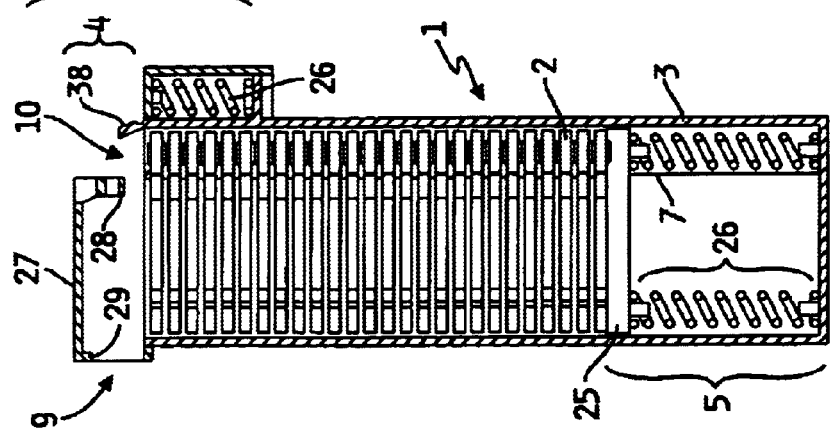

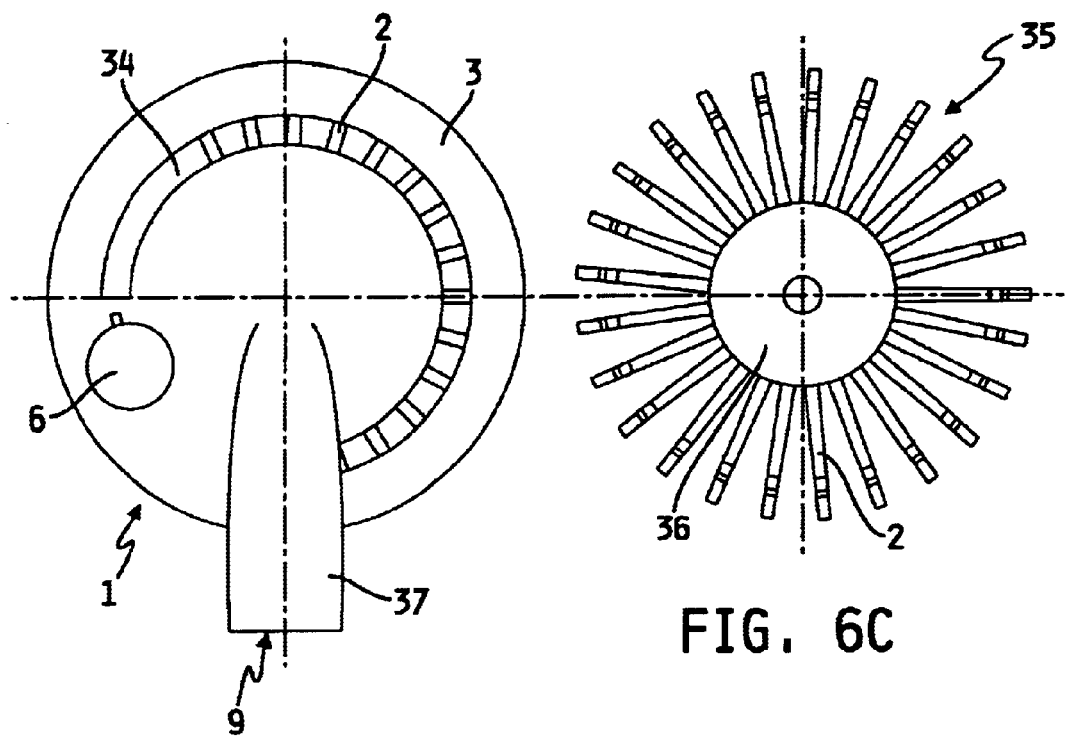
FIG. 6A
FIG. 6C
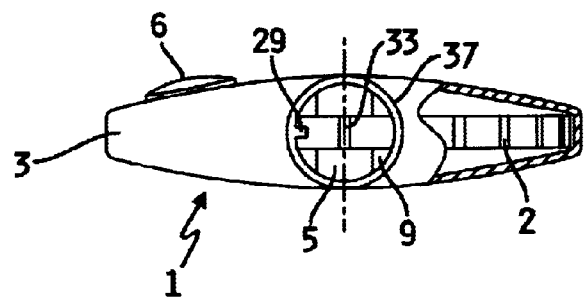
FIG. 6B
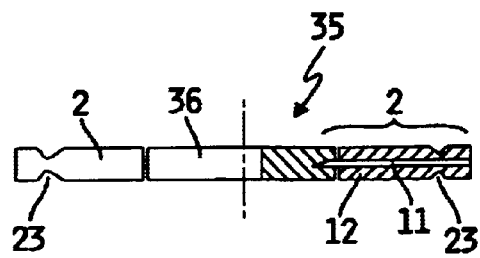
FIG. 6D

LANCET DISPENSER

RELATED APPLICATION

This application claims priority from Application No. 198 40 8560 filed Sep. 7, 1998, in the Federal Republic of Germany, incorporated herein by this reference.

BACKGROUND AND SUMMARY

The invention concerns a system which is suitable for obtaining a body fluid, in particular blood, from a body region of a person to be examined, wherein the system contains a lancing device, two or several lancets and a lancet magazine for storing two or several lancets. The invention additionally concerns a lancing device, lancets and a lancet magazine which are suitable for use in a system according to the invention and it concerns a special method for removing a lancet from a lancet magazine.

The examination of blood samples in clinical diagnostics enables an early and reliable detection of pathological states and the specific and well-founded monitoring of body states. Medical blood diagnostics always requires the collection of a blood sample from an individual to be examined. Whereas several millilitres of blood are collected from a person to be examined by venipuncture for analysis in hospitals and by physicians in private practice in order to carry out many laboratory tests, nowadays only a few microlitres of blood are often sufficient for individual analyses which are specifically for one parameter. Such small amounts of blood do not require venipuncture. On the contrary it is sufficient to obtain blood by pushing a sterile, sharp lancet through the skin e.g. into the finger pad or earlobe of the person to be examined in order to collect a few microlitres of blood for the analysis. This method is particularly suitable when it is possible to carry out the analysis of the blood sample immediately after the blood collection.

Lancets and corresponding instruments (so-called blood withdrawal instruments, blood lancet devices or—as they are referred to in the following—lancing devices) which enable a substantially pain-free and reproducible blood collection are available especially in the so-called home-monitoring field i.e. where medical laymen themselves carry out simple analyses of the blood especially for the regular blood collection by diabetics which has to be carried out several times daily to monitor the blood glucose concentration. Furthermore the use of lancets with lancing devices which lower the psychological threshold when lancing one's own body is of particular importance for children affected by diabetes who depend on regular blood glucose tests. Examples of lancets and lancing devices are the commercially available instruments and lancets Glucolet® from the Bayer AG Company and Softclix® from the Boehringer Mannheim GmbH. Such lancets and instruments are for example the subject matter of EP-A 0 565 970, U.S. Pat. No. 4,442,836 or U.S. Pat. No. 5,554,166.

In the systems that are available at present the lancets for use in lancing devices are usually provided in a loose form. For each lancing process the user manually removes a lancet from a pack, for example a cardboard box or a tube loosely filled with a plurality of lancets in a disordered arrangement. Subsequently the lancing device is prepared for holding the lancet for example by unscrewing or pulling off a protecting cap whereby the lancet holder of the lancing device is exposed. The lancet holder serves on the one hand to hold the lancets, on the other hand it guides the lancet in the actual lancing process. The lancet removed from the pack is manually inserted into the lancet holder of the lancing device and immobilized there. Then the protective cover which surrounds the lancet tip and protects this and the user, must be manually removed from the lancet. Subsequently the lancing device is sealed again with its protecting cap. The protecting cap ensures that the lancet is no longer accessible from outside. It usually has an opening through which the lancet tip can pass during the actual lancing process. Finally the lancing device is tensioned and is available for the lancing process for drawing blood.

The many manual operating steps are felt to be disadvantageous by the user and are particularly problematic when perception is limited in a hypoglycaemic state. Moreover the user will be encouraged to use a once inserted lancet several times for lancing and drawing blood. This is unacceptable for hygienic reasons and the repeated use of lancets also leads to increasing pain for the user since the lancets are designed as disposable articles and rapidly become blunt. Furthermore with the lancing devices and lancets of the prior art there is a risk that lancing devices will be used with lancets that do not fit or that the lancets will be inserted improperly into the lancing devices. Furthermore a user can be accidentally injured when the lancets and lancing devices are used improperly.

There have therefore been no lack of attempts to eliminate the said disadvantages. Lancing devices are known from the US patent documents U.S. Pat Nos. 3,030,959, 4,794,926, 5,035,704 and 5,152,775 in which several lancets are stored and which can use these individually and in succession for lancing processes. Lancets that are linked together are known from U.S. Pat No. 5,514,152 and WO 98/14125 which lancets can be inserted together in a type of lancing device. However, the designs proposed in these documents can only partially solve the said problems and themselves cause some new disadvantages such as a complicated construction of the lancing device and/or lancets, lack of hygiene and/or sterility and inadequate user convenience.

The object of the invention is to eliminate the disadvantages of the prior art. In particular it is an object of the present invention to reduce the number of manual operating steps required to insert a lancet into a lancing device and thus to increase the operating convenience for the user. Furthermore an object of the invention is to ensure that the lancet can be inserted in the lancing device without mistakes and to increase the safety for the user when using the lancing device and lancet especially in hypoglycaemic states.

The object is achieved by the subject matter of the invention as characterized in the patent claims.

The invention concerns a system that is suitable for collecting a body fluid, in particular blood from a body region of a person to be examined containing a lancing device which is suitable for holding a lancet, a lancet magazine for storing two or several lancets which has a transport device for the lancets and an opening into which the lancing device can be inserted to remove a lancet from the lancet magazine, and two or several lancets.

The system according to the invention is suitable for collecting a body fluid, in particular blood from a person to be examined. In this process the lancet that is held, guided and driven by the lancing device pierces the skin of this person to a defined puncture depth and thus forms a tiny wound. A drop of the body fluid, in particular blood of usually a few microlitres up to a maximum of 100 microlitres volume collects on the surface of the wound. The body fluid is preferably used immediately after the collection for a diagnostic examination. However, the body fluid sample can also be used for a later examination.

In particular the system according to the invention can be used to collect capillary blood from a body region such as e.g. a finger pad or an earlobe. The system can be used by the person to be examined himself, for example a diabetic who wishes to determine his blood glucose content and also by a third person e.g. a doctor or a nurse to collect blood samples from a patient.

The system according to the invention contains a lancing device, lancets and a lancet magazine whose form and function are matched to one another to achieve an optimal interaction between the individual system components. The individual components and their interaction is elucidated in more detail in the following.

Lancet Magazine

The central component of the system according to the invention is a lancet magazine. It serves to hold, store and provide the lancets and makes the functional connection between the lancets and lancing device. In order to fulfil these purposes the lancet magazine has a housing in which the lancets are stored, a removal position for a lancet and optionally means which hold a lancet in the removal position, a device which enables manual or automatic transport of the lancets into the removal position, an opening into which the tip of the lancing device can be inserted in order to remove a lancet and which optionally contains means for guiding the lancing device, optionally an additional opening which is opposite to the opening for the lancing device which allows the protective sheath of the lancet needles can be removed after they have been withdrawn by the lancing device from the inside of the lancet magazine and optionally a closable opening through which the lancets magazine can be filled with lancets.

The lancet magazine is preferably not primarily used to maintain the sterility of the lancets. This is preferably achieved by suitable constructional measures on the lancet itself, for example by sealing the lancet tip in a removable, tight plastic protective sheath.

The housing of the lancet magazine is manufactured from a metal for example aluminium or a plastic e.g. polypropylene or polyethylene. The housing is preferably manufactured by injection moulding from injection-mouldable material, in particular plastic. The housing can in principle have any shape that is suitable for the function of the lancet magazine. It has turned out to be preferable for the lancet magazine to either have the shape of an elongate, flat cuboid i.e. similar to a packet of cigarettes, or the shape of a flat quadratic, polygonal or round disk e.g. like a powder tin. Of course the edges and corners of the housing can be rounded for design or ergonomy purposes. The dimensions of the lancet magazine are essentially determined by the size of the lancets and the number of the lancets that are to be stored. According to the invention at least two lancets can be stored in the magazine. The lancet magazine preferably serves to store 10 to 200 lancets. It particularly preferably contains 20 to 50 lancets.

In a preferred embodiment the lancet magazine has a is flat, elongate cuboid shape. The length and width of the short, narrow surfaces correspond to the dimensions of a single lancet; the width of the long, narrow surfaces correspond to the width of the lancet and their length corresponds to at least the sum of the heights of the lancets that are to be accommodated in the magazine. This accordingly results in the dimensions of the large cuboid surfaces. In this preferred embodiment the lancets are stacked pair-wise in the magazine either in contact next to or above one another or opposite to one another e.g. head to head and can be present individually and also connected detachably to one another to form a set of lancets for example by glueing or welding the individual lancets at their points of contact i.e. similar to the manner in which staples adjoin one another to form a set or they are connected by thin plastic cross-pieces.

In an alternative equally preferred embodiment, the lancet magazine has a flat quadratic, regular or irregular, polygonal or round disk shape. In this embodiment the lancets are preferably arranged radially in a plane around a central axis where the lancet tips are particularly preferably inserted into a common central plastic disk and the lancets are thus linked together to form a lancet disk. Furthermore the lancet tips are kept sterile in this manner.

Independent of the external shape of the lancet magazine—whether cuboid or disk shaped—the lancet magazine according to the invention has a removal site or removal position for a lancet. A lancet is moved into this position with the aid of a transport device located in the magazine in order to be removed by the lancing device. After a lancet has been removed from the magazine, the transport device serves to transport the next i.e. the lancet in the magazine which was originally adjacent to the lancet that has been removed, to the removal position of the magazine. This transport of the next lancet to the removal position can be carried out automatically by the transport device so that there is always a lancet in the removal position provided the magazine contains lancets, or the transport of the next lancet is not automatically triggered by the removal of a lancet but rather manually by the user. The transport mechanism can be coupled to a counting device which shows the user how many lancets from the magazine have already been used or how many lancets are still stored in the magazine.

In a preferred embodiment the transport device can move up all remaining lancets in the magazine. However, in another embodiment it was also possible to only transport one lancet to the removal position and preferably the next in position.

In a preferred embodiment the lancets are manually brought into the removal position with the aid of a slide that is operated from outside. The slide can be moved continuously towards the removal position or in discrete steps, for example with stops, using for example an operating knob and thus transport the lancets contained in the magazine. In this connection a side surface of the lancets preferably lies wholly or partially on the part of the slide that is located in the magazine.

In a further preferred embodiment the lancets are moved into the removal position with the aid of an automatic feed system, for example by means of a linearly movable plate driven by spiral springs in the case of the cuboid magazine or by means of a coiled spring which acts on the lancets in such a way that they make a guided, planar circular movement in the case of the disk-shaped magazine. The automatic feed system can also be driven by a motor.

In the case of an automatic feed system the transport movement of the lancets in the magazine can be triggered manually for example by operating a switch. However, the transport movement can also be started automatically by the removal of a lancet from the magazine.

Stops as well as guide grooves and guide pins or guide flanges may be present in the inner magazine walls as well as on the lancets which ensure a precise positioning of the lancets especially during transport of the lancets into the removal position.

In an additional particularly preferred embodiment of the lancet magazine according to the invention, the lancets are brought into a preliminary removal position with the aid of a first transport device from which they are moved into the final removal position with the aid of a second transport mechanism. The first transport device can be a manually operated slide as well as an automatic feed system. In this particularly preferred embodiment the second transport device is a movable part of the lancet magazine, for example a linearly movable part of the housing supported on one or several springs. Pressure on this part of the housing moves it towards a lancet located in the preliminary removal position whereby this lancet is gripped with a gripping system for example by means of a barbed system which is optionally mounted on flexible tongues or by means of magnets. When the movable part of the magazine glides back, the lancet is transported into the final removal position and held there by the gripping system until the lancet is removed from the magazine with the aid of a lancing device.

A preferably sealable opening in the magazine is located in the area of the removal position into which at least the tip of the lancing device can be inserted in order to remove a single lancet from the inside of the lancet magazine. The geometry and size of the opening depend on the corresponding dimensions of the lancing device. The lancing device and opening preferably fit like a lock and key to ensure an unequivocal and precise alignment of these two system components during the removal process. In order to facilitate the insertion of the lancing device into the opening, the opening can have a conical or funnel shape so that it, is larger towards the outside than is necessary to receive the tip of the lancing device. It is also possible that the tip region of the lancing device which is inserted into the lancet magazine is tapered to facilitate the insertion.

In a preferred embodiment a guide pin is provided in the interior of the magazine opening which engages in a corresponding guide groove in the tip of the lancing device. Of course the pin can also be located on the lancing device in which case the guide groove is then in the opening of the magazine.

When the lancing device is inserted into the magazine or removed from the magazine i.e. when movements are made which can be regarded as essentially linear and parallel to the longitudinal axis of the lancing device, the guide pin and guide groove particularly preferably serve to automatically and mechanically at least partially rotate the lancing device around its longitudinal axis. The lancet is rotated around its longitudinal axis by this rotary motion of the lancing device or a of part of the lancing device which twists off the protective sheath on the lancet tip which in this case is stored in the magazine such that it cannot rotate. Hence the lancet is removed from the magazine without its protective sheath which remains at first in the magazine and can optionally be removed e.g. ejected from the magazine via an additional opening that is preferably opposite to the opening for the insertion of the lancing device.

The lancet magazine can be designed as a single use magazine (disposable magazine), or it can have means which allow the magazine to be filled with lancets. For example part of the housing of the lancet magazine can be movable and thus serve as a door or lid through which the magazine can be filled with lancets. It is also possible that part of the magazine is designed as a drawer into which lancets can be placed and inserted into the magazine.

In a preferred embodiment the lancet magazine has means which allow the actual contents of lancets to be seen from outside. For example the housing of the lancet magazine can be completely or partially transparent. It is also possible to determine the filling level by means of the relative position of a slide which may be optionally present for example by having stops in the slide position and simultaneously a scale of the degree of filling.

Lancets

Lancets that are suitable for the system according to the invention are in principle described in the prior art for example in EP-A 0 565 970. Commercially available lancets such as the Softclix® II lancet from the Boehringer Mannheim GmbH are also suitable for preferred embodiments of the system according to the invention.

Preferred lancets according to the invention have a needle made of metal, ceramics or plastic, one end (the tip) of which is pointed for example by a grinding process. In a preferred embodiment the rear part of the lancet needle facing away from this tip is usually wholly or partially enclosed in a lancet body made of plastic. It is usually manufactured by positioning the lancet needle in a plastic injection mould and injecting on the lancet body. In this process a protective sheath made of plastic can also be injection moulded at the same time over the tip of the lancet. The protective sheath can be present detached from the lancet body. It is, however, also possible that the protective sheath and lancet body form a unit in which case a predetermined breaking point is provided between the protective sheath and the lancet body so that the protective sheath can be cleanly removed from the lancet.

However, lancets are also suitable according to the invention which do not have a sheath for the lancet needle. For simplicity the term "lancet" is used in the following for all variants i.e. lancet needles with and without a lancet body.

The preferred lancet for the system according to the invention contains a metal needle with a sharp point which in the process of pricking the person to be examined pierces his skin to obtain blood. The metal needle is preferably held by a lancet body i.e. a plastic or metal body which facilitates the handling of the needle.

Suitable lancets for the system according to the invention preferably contain a metal needle which is at least partially encased in a plastic body in which the plastic body preferably contains means which enable the lancet to be gripped and held by a lancing device. For example the plastic body can have a pair of opposed V-shaped recesses, circular notches or funnel-shaped indentations into which the complementary shaped barbs or elastic tongues of the lancet holder of the lancing device engage and can thus grip the lancet. Of course there may also be projections on the lancet body which can engage in corresponding recesses in the lancet holder of the lancing device.

In a preferred embodiment there are additional means present on the plastic body which prevent the lancet from being displaced or even pushed out of the lancet magazine by the lancing device during the gripping process. For example the lancet body can be provided with pins or ribs which engage in corresponding guide grooves in the lancet magazine and thus is held in its relative position to the inserted lancing device during the gripping process. Of course it is also possible that the lancet body has the groove(s) and the magazine has one or several corresponding ribs which engage in the groove(s).

In the magazine the lancet tip is preferably protected by a protective sheath for example a plastic sheath. The protective sheath serves on the one hand to protect the lancet tip from external damaging effects such as e.g. bending or contamination, which would mean a loss of the sterility of the lancet tip and, on the other hand, to protect the user from being accidentally pricked by the lancet for example when the magazine is filled with lancets. The protective sheath can be connected to the plastic body of the lancet or can be separate from this, the connected variant being preferred. The protective sheath can be a solid plastic which completely and contiguously surrounds the lancet tip or can be in the form of a hollow body moulded around the lancet tip. Each lancet can have an individual protective sheath like those that have previously been commonly used for lancets of the prior art. It is, however, also possible in a preferred embodiment that the tips of several lancet tips or all lancets present in the lancet magazine are inserted into a common plastic body, in particular a common central plastic disk which serves as a protective sheath for the lancet tips.

For the particularly preferred variant of the lancet magazine according to the invention in which the lancets can be refilled in the magazine, it has proven to be advantageous when the individual lancets are present linked together to form a set of lancets. Such a set of lancets particularly preferably contains two or several lancets which are loosely connected together for example in the region of their tips or lancet bodies. This can on the one hand be achieved by the method described above i.e. several lancet tips or the tips of all lancets present in the magazine are inserted in a common, preferably centrally disposed, plastic body, but on the other hand it can also be achieved by detachably connecting the plastic bodies or protective sheaths of individual lancets e.g. by glueing. The connection can be made by adhesive tapes as is for example common for electronic components or directly as is for example known for staples. Furthermore it is also possible to connect the lancet bodies together by plastic cross-pieces or to detachably link the lancets together via a common holder which is for example in the form of a rail or a link chain.

Lancing Device

Numerous types of lancing devices are known from the prior art for example from EP-A 0 565 970 and are commercially available e.g. under the name Softclix® II from Boehringer Mannheim GmbH. With reference to the prior art and in particular to EP-A 0 565 970, it is therefore unnecessary to elucidate in more detail the general features and function of such lancing devices or blood lancet devices as they are also known.

Elongate cylindrical lancing devices are preferred according to the invention i.e. those which essentially have the shape of a fountain-pen. These lancing devices have in their interior a mechanism which guides the lancet in the lancing process towards and, after the lancing, away from the desired lancing site in the skin of the person to be examined. Usually this mechanism is driven by a tensioned spring which is manually tensioned which is why suitable tensioning devices must be present for this embodiment. A triggering button can be present on the outside of the lancing device to trigger the mechanism.

Lancing devices in a fountain-pen shape have a grip body which enables the lancing device to be handled comfortably and usually most of the mechanism described above is accommodated in its interior. Furthermore the operating knobs to trigger the thrust mechanism and optionally to eject used lancets from the lancing device are often present in the region of the grip body.

The lancet holder is preferably located at one end of the lancing device which is referred to as the tip of the lancing device. This can be concealed below a removable protecting cap. For the invention it is important that the lancet holder of the lancing device contains means which enable a lancet to be gripped and which are thus suitable for removing a lancet from the lancet magazine. For this purpose the lancet holder can be inserted into the lancet magazine through its opening in order to remove a lancet. The lancet holder is thus the tip of the lancing device which is inserted into the lancet magazine in order to withdraw a lancet. Its exact form results, on the one hand, from the shape of the lancets which are held in it and which should be gripped by it and, on the other hand, on the opening of the lancet magazine into which it is inserted. The lancet holder of the lancing device preferably corresponds to that which is known from EP-A 0 565 970.

For the system according to the invention composed of lancing device, lancet magazine and lancets it has proven to be advantageous that the part of the lancing device which is inserted into the lancet magazine to remove a lancet has a guide groove or a guide pin which can interact with a corresponding device in the opening of the lancet magazine. This ensures that the lancing device and magazine can be joined without mistakes. Furthermore, as described above an appropriate shape of the groove—whether it is in the lancing device or in the opening of the magazine—can force a rotation of the lancing device around its longitudinal axis so that it rotates when it is inserted into the magazine or when it is removed from the magazine. In this process the lancet in the lancet holder is also rotated around its longitudinal axis and thus the protective sheath around the lancet tip is twisted off. This ensures that the lancet is present in the lancing device without a protective sheath. In this manner it is not necessary to manually twist off the protective sheath and the risk of injury to the user is reduced. Moreover the number of movements that are necessary to place a lancet in the lancing device is minimized and thus the entire procedure is simplified for the user.

A further subject matter of the invention is a lancet magazine for storing two or several lancets which is suitable for use in the system according to the invention. Such a lancet magazine has already been described above in connection with the system according to the invention.

An additional subject matter of the invention is a lancet containing a metal needle that is partially encased in a plastic body which is suitable for use in the system according to the invention. Such a lancet has already been described above in connection with the system according to the invention.

Moreover the invention concerns a lancing device which is suitable for use in the system according to the invention. Such a lancing device has already been described above in connection with the system according to the invention.

Finally a further subject matter of the invention is a process for removing a lancet from a lancet magazine in which a lancet located in the lancet magazine is manually or automatically transported into a removal position in the interior of the lancet magazine and a lancing device is partially inserted into an opening provided for it in the lancet magazine. When the lancing device is partially inserted, it automatically grips the lancet that is in the removal position. Finally the lancing device with the gripped lancet is removed from the lancet magazine.

Preferably either during insertion of the lancing device into the lancet magazine i.e. when the lancet is gripped by the lancing device or when the lancing device is removed from the lancet magazine, the lancing device and thus also the lancet is rotated so that the protective sheath made of plastic which protects the needle tip of the lancet is twisted off. This rotation is particularly preferably achieved automatically by appropriate means in the lancing device as well as in the lancet magazine for example by a curved guide groove on the one side and a corresponding guide pin on the other side.

The advantages of the invention can be summarized as follows:

The system according to the invention composed of lancet magazine, lancets and lancing device simplifies lancet replacement for the user, reduces the time required and thus increases his readiness not to use lancets that have already been used once. This minimizes the risk of infection and helps to reduce pain during blood collection. Furthermore it facilitates the handling of the system in hypoglycaemic states.

Since the user no longer has to separately hold the lancets in his hand, the lancets can be made considerably smaller than the previously common lancets which reduces the amount of material required for their manufacture. In addition disposal of the lancets creates less waste. Finally the whole system can,be kept more compact so that it is easier for the user to take with him.

The lancets in the lancet magazine are offered to the lancing device in a well-defined orientation thus excluding an insertion in an incorrect orientation.

The lock-key principle of the lancet magazine and lancing device rules out the use of unsuitable lancets for the lancing device.

The lancet magazine as a reusable system component can be filled with new lancets either by the manufacturer, the distributor or the consumer. The lancets themselves can be put on the market with a minimum of packaging in a space-saving and waste-saving manner.

BRIEF DESCRIPTION OF THE DRAWINGS

The invention is further elucidated by the following figures.

FIG. 4 shows schematically a side-view of a further preferred embodiment of a lancet magazine according to the invention in which a side wall has been removed to enable a view of the interior of the magazine and the lancets contained therein (partial FIG. A), schematic side and front-views of those parts of a preferred lancet dispenser and of a corresponding lancing device (partial FIG. B) which interact with one another to remove the lancet, as well as a top-view (partial FIG. C) and a side-view (partial FIG. D) of a preferred embodiment of a lancet which can be accommodated in the lancet magazine according to FIG. 4A.

FIG. 6 shows schematically on the basis of four partial FIGS. (A to D) a further preferred embodiment of a lancet magazine in a top-view (A) and from the front (B) as well as a suitable set of lancets for this lancet magazine that are detachably connected together also in top-view (C) and from the front (D). In this connection the views from the front (B,D) are partially cut out in order to illustrate details of the construction.

The numbers in the FIGS. denote:

Figure 1:
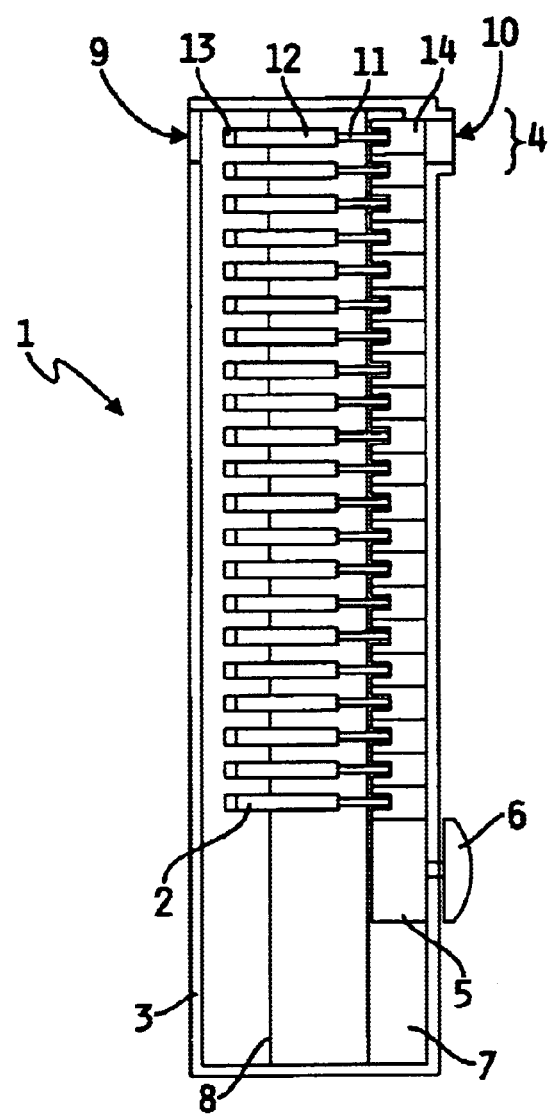
FIG. 1 shows schematically a side-view of a preferred embodiment of a lancet magazine according to the invention in which a side wall has been removed to enable a view of the interior of the magazine and the lancets contained therein.

| | |
|---|---|
| 1 | lancet magazine |
| 2 | lancet |
| 3 | housing |
| 4 | removal site |
| 5, 5' | transport device |
| 6 | operating knob for the transport device 5 |
| 7 | guide groove for the transport device 5 |
| 8 | stop |
| 9 | opening to insert the lancing device 15 |
| 10 | opening to eject the protective sheath 14 |
| 11 | metal needle |
| 12 | lancet body |
| 13 | pin |
| 14 | protective sheath |
| 15 | lancing device |
| 16 | grip body |
| 17 | tip |
| 18 | protective cap |
| 19 | lancet holder |
| 20 | flexible holding tongue with barbs |
| 21 | ejector |
| 22 | funnel-shaped notch in the lancet body 12 |
| 23 | V-shaped recess in the lancet body 12 |
| 24 | projection on the protective sheath 14 |
| 25 | plate |
| 26 | spiral spring |
| 27 | movable housing member |
| 28 | gripper system |
| 29 | guide pin |
| 30 | guide groove |
| 31 | lancet 2 in the preliminary removal position |
| 32 | holding device |
| 33 | lancet 2 in the final removal position |
| 34 | viewing window |
| 35 | set of lancets |
| 36 | plastic disk |
| 37 | insertion socket |
| 38 | flexible tongue |

DETAILED DESCRIPTION OF THE DRAWINGS

A diagram of a side-view of a particularly preferred embodiment of a lancet magazine (1) is shown in FIG. 1 in which a side wall of the housing (3) has been removed to enable a view into the lancet magazine (1) and of the lancets (2) contained therein. The lancet magazine (1) has essentially an elongate, flat cuboid shape in which the lancets (2) are arranged linearly next to one another each in pair-wise contact. The lancets can be manually pushed to the removal site (4) with the aid of a transport device (5) for which an operating knob (6) for the transport device (5) is provided on the outside of a long, narrow side of the lancet magazine (1). The transport device (5) can be moved continuously or discontinuously, for example with stops, with the aid of the operating knob (6). The position of the operating knob (6) allows the actual filling level of the magazine (1) to be displayed. As best shown in FIGS. 1, 3, and 4, lancets (2) are removed from the lancet magazine (1) in a direction that is substantially parallel to a longitudinal axis of the lancing device (15) and transport device (5) moves in a direction substantially perpendicular to the longitudinal axis of the lancing device (15).

A guide groove (7) is contained within the lancet magazine (1) in which the transport device (5) and the protective sheath (14) of the lancets (2) are guided. The protective sheaths (14), the transport device (5) and the guide groove (7) are appropriately matched in size and shape.

A stop (8) is also located in the interior of the housing (3) of the lancet magazine (1) which, together with the pin (13) of the lancet body (12) ensures that a lancet that is in the removal position (4) cannot be pushed out of the opening (10) of the lancet magazine (1) when a lancing device is inserted through the opening (9).

The guide groove (7) and the stop (8) can also be contained in the side surface of the housing (3) facing the inner side of the lancet magazine (1) which was removed in FIG. 1 to enable a view into the lancet magazine.

Figure 2:
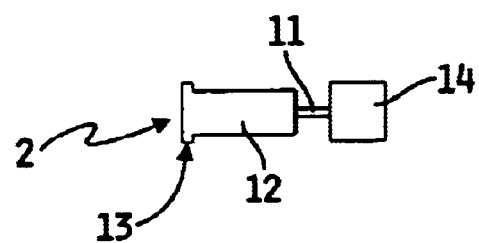
FIG. 2 shows schematically a top-view of a preferred embodiment of a lancet which can be accommodated in a lancet magazine according to FIG. 1.

A lancet (2) is shown in FIG. 2 which can be accommodated in a lancet magazine (1) according to FIG. 1. Whereas the lancet (2) in FIG. 1 is shown schematically in a side-view, a schematic top-view of a lancet (2) is shown in FIG. 2. The lancet (2) is composed essentially of a metal needle (11) with a tip that is surrounded by a protective sheath (14). This protective sheath (14) must be removed from the lancet (2) before the lancet (2) is used to draw blood. The lancet (2) additionally contains on that side which is opposite to the protective sheath (14), a lancet body (12) which contains a pin (13) on both sides. This, together with the stop (8) in the housing (3) of the lancet magazine (1), ensures that a lancet (2) located at the removal site (4) cannot be pushed out of the lancet magazine (1) when a lancing device is inserted. The lancet body (12) and the protective sheath (14) are preferably manufactured from an injection-mouldable plastic.

FIG. 3 shows schematically on the basis of 7 partial FIGS. (A to G) how a lancet (2) which is at the removal position (4) of a lancet magazine (1) is removed from the lancet magazine (1) with the aid of a lancing device (15). The lancing device (15) essentially has a fountain-pen shape. Its essential components are a grip body (16), a tip (17) and a protective cap (18). The movable mechanical components of the lancing device (15) that are required for the lancing movement are accommodated in the grip body (16). These substantially correspond to the prior art, for example, EP A-0565 970 and are not intended to be elucidated in more detail here. The lancet holder (19) is accommodated in the tip (17) which is exposed when the protective cap (18) is pulled off or unscrewed from the lancing device (15). Essential features of the lancet holder (19) of the present particularly preferred embodiment of a lancing device (15) are the flexible holding tongue (20) with a barb and the ejector (21) since these components of the lancet holder (19) interact directly with the lancet (2) in the lancet magazine (1).

Figure 3A:
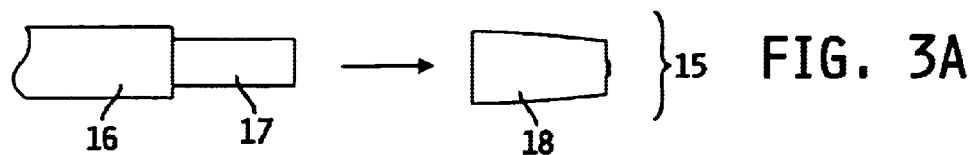
FIG. 3 shows schematically how lancets can be removed from the lancet magazine according to FIG. 1 using a lancing device on the basis of seven partial FIGS. (A to G).
Figure 3B:
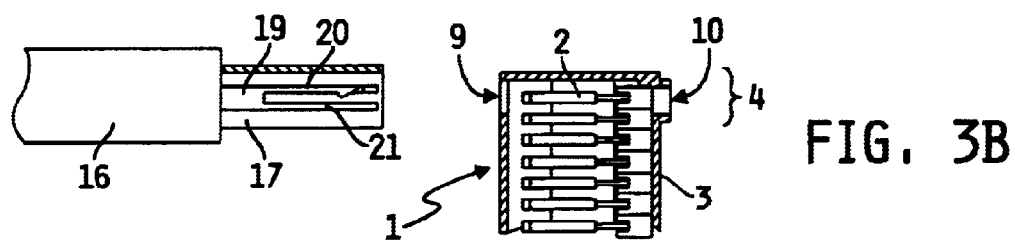
Figure 3C:
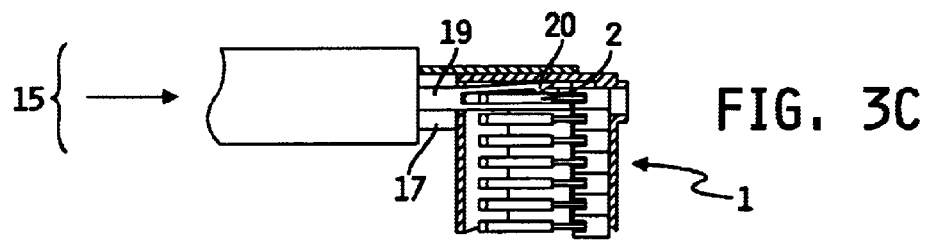
Figure 3D:
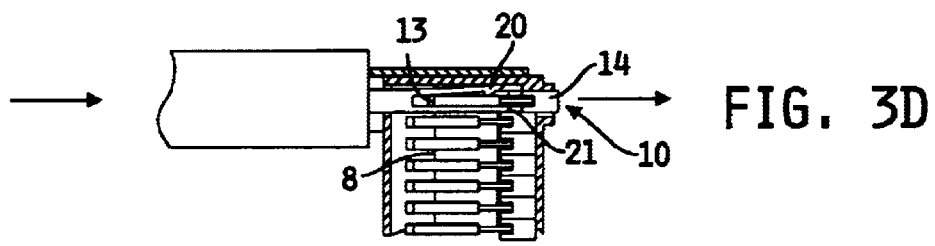
Figure 3E:
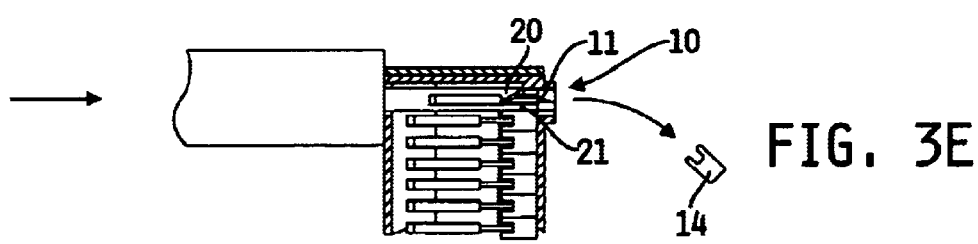
Figure 3F:
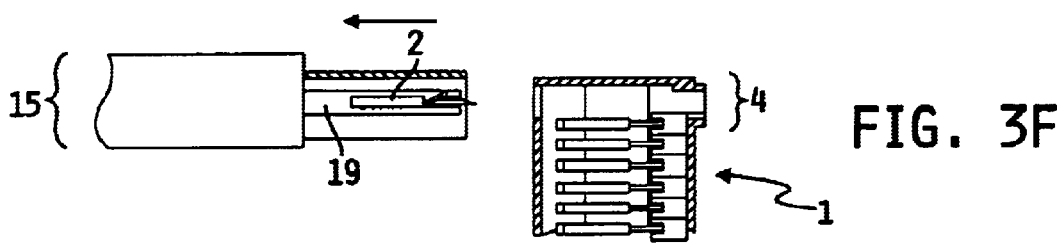
Figure 3G:
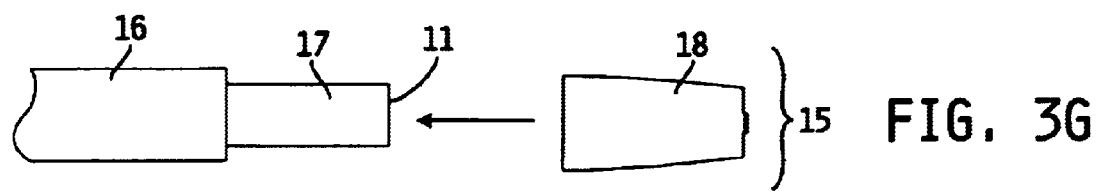

After the protecting cap (18) has been removed from the lancing device (15), the tip (17) of the lancing device is exposed (FIG. 3A). The lancing device (15) is moved with its tip (17) first towards the lancet magazine (1) in which a lancet (2) is located at the removal position (4) (FIG. 3B). The tip (17) of the lancing device (15) has a recess which enables the tip (17) to be pushed over the lancet magazine (1). As a result the lancet holder (19) is inserted through the opening (9) into the lancet magazine. In this process the flexible holding tongue (20) glides over the lancet (2) located at the removal position (4) which slightly bends the holding tongue (20) upwards (FIG. 3C). As the lancet holder (19) is further inserted into the lancet magazine (1), the lancet is pushed by the ejector 21 towards the opening (10) until the pin (13) of the lancet body (12) rests on the stop (8) thus preventing further displacement of the lancet (2) (FIG. 3D). When the lancet holder (19) is pushed farther into the lancet magazine (1), the ejector 21 no longer pushes the whole lancet (2) but only the protective sheath (14) towards the opening (10). When the lancet holder (19) is completely inserted into the lancet magazine (1), the ejector (20a) separates the protective sheath (14) from the lancet tip and the protective sheath falls out of the opening (10). At the same time the barb of the flexible holding tongue (20) grips in front of the lancet body (12) and thus holds the lancet (2) in the lancet holder (19) (FIG. 3E). When the lancing device (15) is removed from the lancet magazine (1), the lancet (2) which is located in the lancet holder (19) is also removed from the magazine (1). This makes room at the removal position (4) for a lancet (2) to be advanced which can be manually pushed to the removal position (4) with the aid of the transport device (5) traveling in a direction substantially perpendicular to the longitudinal axis of the lancing device (15) (FIG. 3F). After the process of removing the lancet (2) from the lancet magazine (1), the lancing device (15) must be sealed with the protecting cap (18). In this process the lancing device (15) can be automatically tensioned by rotation of the protecting cap (18). It is thus available for collecting blood.

FIG. 4A shows a further particularly preferred embodiment of the lancet magazine (1) according to the invention in a side-view in which the lancet magazine (1) is shown partially in section. The lancet magazine (1) has essentially an elongate flat cuboid shape. Like the embodiment of FIG. 1, the lancets (2) in this case are also arranged essentially linearly next to one another and in pair-wise contact. The lancets (2) are transported automatically towards the removal position (4) by a transport device (5) traveling in a direction substantially perpendicular to the longitudinal axis of the lancing device (15). In the embodiment of FIG. 4A. transport device (5) is essentially composed of a plate (25) and two spiral springs (26) which drive this plate (25). A second transport device (5') is provided in the region of the removal position (4). This is essentially composed of a movable housing member (27) which is held in the resting position shown by a spiral spring (26). In the region of the transport device (5') there are also the openings (9) for inserting the lancing device as well as the opening (10) to eject the protective sheath (14) of the lancet (2) which also makes use of the flexible tongue (38) which is movably attached to the housing (3) of the lancet magazine (1). A further component of the transport device (5') is a gripper system (28) which grips the top lancet (2), i.e. the lancet that is nearest to the removal position (4), when the transport device (5') is operated.

Detailed drawings of schematic views of the lancing device (15) in a side and front view as well as those parts of the lancet magazine (1) into which the lancing device (15) can be inserted to remove a lancet (2) are shown in FIG. 4B. Only that part of the lancing device (15) which is relevant to the invention is shown at the top left of FIG. 4B like the lancing device (15) from FIG. 3A. Also in this case the other functional components correspond to the prior art. The lancing device (15) comprises a grip body (16) and a tip (17) in which a lancet holder (19) is housed which in turn has a flexible holding tongue (20). The side-view of these components of the lancing device (15) are shown in a partial section in FIG. 4B. A top-view from the front of the lancing device (15) is shown on the right-hand side next to the side-view in FIG. 4B. The top-view illustrates the relative position of the aforementioned components. In addition the guide groove (30) is shown that is provided in the tip of the lancing device (17).

A frontal detailed view of the opening (9) of the lancet magazine (1) is shown in FIG. 4B below this frontal view of the lancing device (15). On the right is a side-view of the lancet magazine (1) in a partial section. The gripper system

(28) and the guide pin (29) are shown in particular in the frontal view of the opening (9) of the lancet magazine (1). The gripper system (28) is composed of two movable tongues provided with barbs which, when the movable housing member (27) is pressed down, surround and hold a lancet held in the preliminary removal position (31) by a holding device (32) which protrudes sideways as a hemispherical projection from the inner surface of the housing wall of the lancet magazine (1) so that when the spiral spring (26) relaxes this causes the movable housing member (27) to glide back into the starting position taking a lancet (2) into the final removal position (33). In this process the flexible tongue (38) is pressed outwards whereupon it moves back into its resting position which is slightly inclined inwards. When the lancing device (15) is inserted into the opening (9) the guide pin (29) moves in the guide groove (30) in the tip (17) of the lancing device (15). This ensures that the lancing device (15) is inserted in the correct orientation into the opening (9). Furthermore a suitable geometry of the guide groove (30) enables the lancing device (15) to turn around its longitudinal axis when it is inserted through the opening (9) into the lancet magazine (1). In this manner the lancet (2) that is located in the removal position (33) is also rotated around its longitudinal axis. As a result the protective sheath (14) of the lancet (2) as shown in FIGS. 4C and D can be twisted off from the remainder of the lancet (2) to expose the metal needle (11) or its point.

The particularly preferred embodiment of the lancet (2) shown in FIGS. 4C and D is essentially composed of a metal needle (11) which in this case is almost completely surrounded by a plastic body (12). In this case the protective sheath (14) is a component of the plastic body (12) and there is a predetermined breaking point at the site of connection between the protective sheath (14) and the remaining plastic body (12) which allows the protective sheath (14) to be separated when the protective sheath (14) is rotated relative to the plastic body (12). There is a projection (24) on each of the two sides of the protective sheath (14) which serve to detachably connect several lancets (2) to form a set of lancets. In the present preferred embodiment, the lancets (2) are connected together—like staples—by spots of glue on the projections (24).

Means (22, 23) are provided in the lancet body (12) which can engage in parts of the lancet holder (19) in order to hold the lancet (2) firmly in the lancet holder (19). The lancet body (12) in the particularly preferred embodiment of the lancet (2) that is shown, contains a funnel-shaped notch (22) and a pair of opposing V-shaped recesses (23). The barb of the removable tongue (20) of the lancet holder (19) of the lancing device (15) can engage in the funnel-shaped notch (22) and thus hold the lancet (2). The V-shaped recesses (23) can be used with alternative embodiments of the lancet holder (19) of a lancing device (15) that are not shown here.

The lancet magazine (1) of the embodiment shown in FIG. 4 can be opened by the user in order to insert a new set of lancets. The housing of the lancet magazine (1) can be-opened by folding back the transport device (5'). The lancets (2) are inserted into the magazine (1) individually or detachably connected as a set of lancets. In this process the transport device (5) is tensioned again by pressing together the spiral springs (26). Finally the transport device (5') is folded back. The magazine (1) is then ready for use.

Figure 5A:
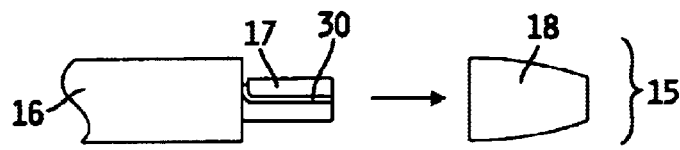
FIG. 5 shows schematically how lancets can be removed from the lancet magazine according to FIG. 4 using a lancing device on the basis of ten partial FIGS. (A to K).
Figure 5B:
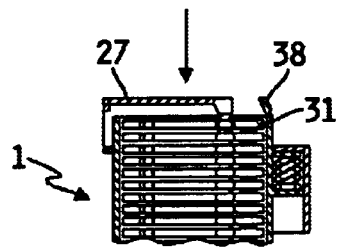
Figure 5C:
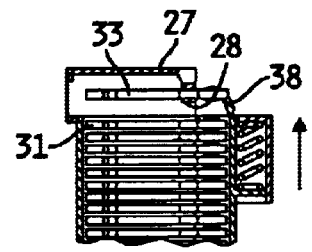
Figure 5D:
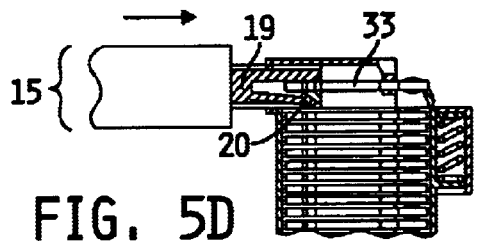
Figure 5E:
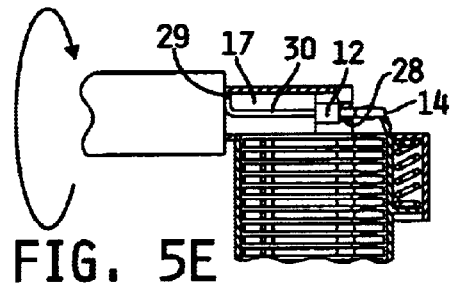
Figure 5F:
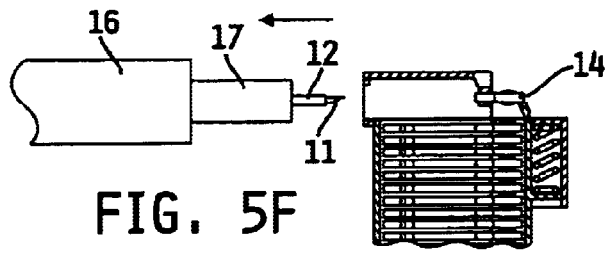
Figure 5G:
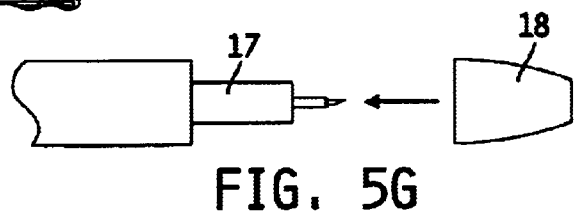
Figure 5H:
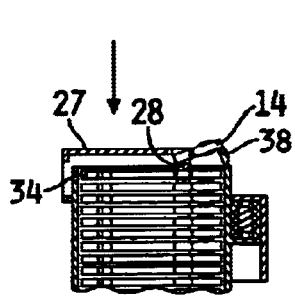
Figure 5I:
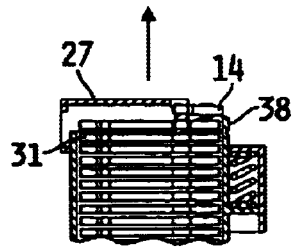

In FIG. 5 ten partial FIGS. (A to K) show—like FIG. 3—how a lancet (2) can be removed from a lancet magazine (1) which corresponds to the particularly preferred embodiment of FIG. 4A with the aid of a lancing device (15):

Before the lancet is removed the protecting cap (18) must be pulled or twisted off the lancing device (15) so that the tip (17) of the lancing device is exposed (FIG. 5A). The lancet which is located in the preliminary removal position (31) and is held there by the holding device (32) is gripped by pressing on the movable housing member (27) of the lancet magazine (1), (FIG. 5B) and is moved into its final removal position (33) when the movable housing member (27) slides back into its original position and the movable tongue (38) is bent outwards where it is held by the gripper system (28). The other lancets in the lancet magazine (1) are pushed forwards by the automatic transport device (5) (cf. FIG. 4A) so that there is again a lancet in the preliminary removal position (31) (FIG. 5C). When the lancing device (15) is inserted into the opening (9) of the lancet magazine (1), the lancet holder (19) grips the lancet (2) located in the final removal position (33) (FIG. 5D). The interaction between the guide groove (30) in the tip of the lancing device (17) and the guide pin (29) in the opening (9) of the housing (3) of the lancet magazine (1) rotates the lancing device (15) around its longitudinal axis when its tip is completely inserted. Since the lancet (2) is already substantially within the lancet holder (19) during the rotation, the lancet (2) is also rotated around its longitudinal axis. The protective sheath (14) is excluded from this rotation since its position is fixed by the gripper system (28) and the flexible tongue (38) and thus cannot rotate. The lancet body (12) is twisted against the protective sheath (14) which breaks the predetermined breaking point between the lancet body (12) and protective sheath (14) (FIG. 5E). When the lancing device (15) is pulled out of the lancet magazine (1), the gripped lancet (2) is also pulled out. In this process the protective sheath (14) is separated from the remainder of the lancet (2) and at first remains in the gripper system (28) (FIG. 5F). The point of the metal needle (11) and parts of the lancet body (12) protrude from the tip (17) of the lancing device (15) in this particularly preferred embodiment. Attachment of the protecting cap (18) covers the exposed point of the metal needle (11) (FIG. 5G). Optionally the lancing device (15) can be tensioned at the same time for example by rotating the protecting cap (18).

Figure 5K:
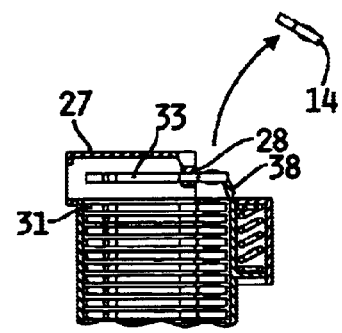

The protective sheath (14) of the lancet (2) which remains in the gripper system (28) is pushed out of the gripper system (28) by the movable tongue (38) when the movable housing member (27) is pressed down again to remove a further lancet (2) from its preliminary removal position (31) (FIG. 5H) and firstly lies loosely on the next lancet (2) to be transported into the final removal position (FIG. 5H) from which it can be easily removed (FIG. 5K).

A further particularly preferred embodiment of the lancet magazine (1) (A, B) and a set of lancets (35) that is suitable for it (C, D) is shown in FIG. 6. The lancet magazine (1) of this preferred embodiment has essentially a flat round disk shape on which a socket (37) is mounted through which a lancing device can be inserted via the opening (9) into the lancet magazine (1) to remove lancets (2). A transparent inspection window (34) is provided on one of the circular sides of the lancet magazine (1) which allows a control of the degree to which the lancet magazine (1) is filled with lancets. The inspection window (34) can be composed of a transparent plastic joined to the housing (3). However, it is also possible that the entire housing (3) is manufactured from a transparent plastic. Alternatively the inspection window (34) can be merely designed as a cut out of the housing (3) which is left open. The transport device (5) can be operated by an operating knob (6) which for example brings lancets into the removal position (3) by means of a spiral spring. A guide pin (29) can in turn be provided in the inside of the opening (9) of the socket (37) which can interact with the guide groove in the lancing device.

A top-view and a view of the front of a set of lancets (35) is shown in FIGS. 6C and D the front view being partially in cross-section. The set of lancets (35) is composed of a plurality of lancets (2) that are arranged radially around a circular central plastic disk (36). The points of the metal needles (11) of the lancets (2) are inserted in the central plastic disk (36). The lancets themselves correspond essentially to the lancets that are shown in FIG. 4C. Also in this case V-shaped recesses (23) are provided in the lancet body (12) which enable an interaction with the lancet holder to a lancing device.

The lancet magazine (1) of the preferred embodiment shown in FIGS. 6A and B can be opened by the user in order to insert a new set of lancets (35). The housing of the lancet magazine (1) can be opened by removing the upper half of the housing i.e. the half provided with an inspection window. The lancets (2) are inserted as a set of lancets (35). The spiral spring of the transport device (5) is tensioned by twisting the inserted set of lancets (35) about its central axis. Finally the removed half of the housing is again attached to the magazine (1) for example by clipping on. The magazine (1) is thus ready to use.

Figure 7A:
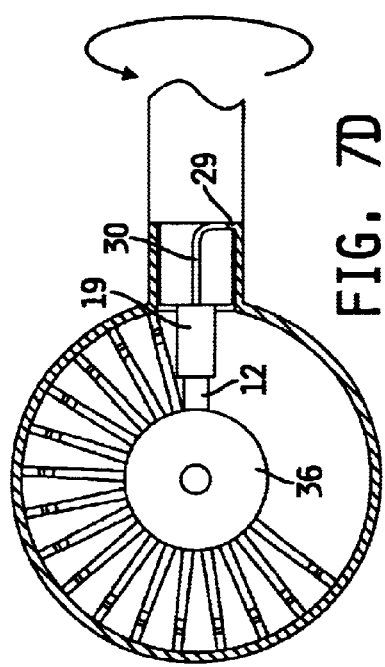
FIG. 7 shows schematically on the basis of six partial FIGS. (A to F) how lancets can be removed from a lancet magazine according to FIG. 6 using a pricking device.
Figure 7B:
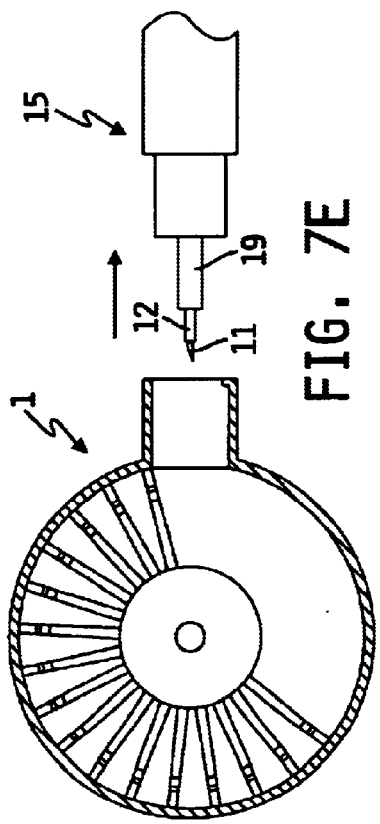
Figure 7C:
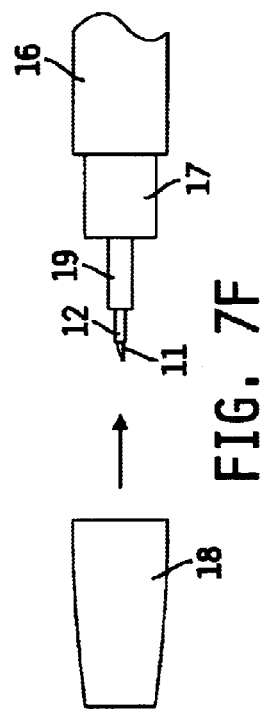
Figure 7D:
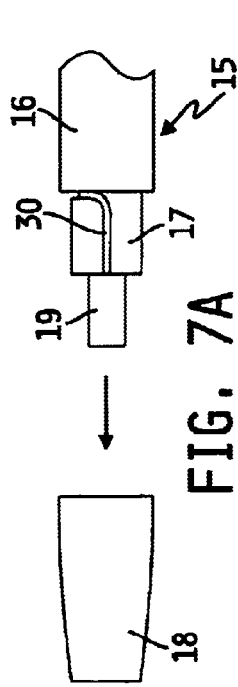
Figure 7E:
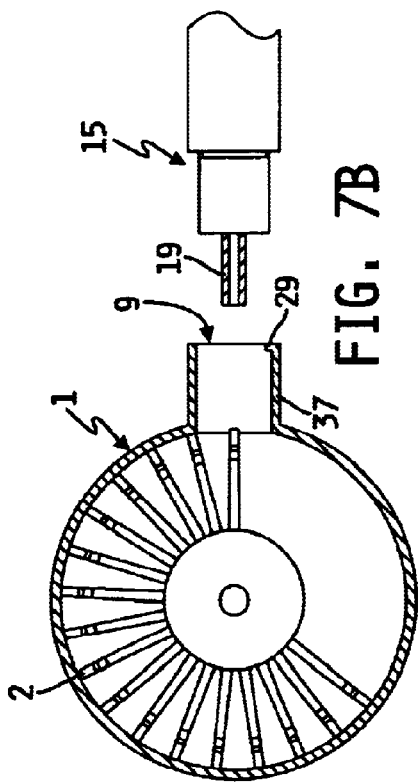
Figure 7F:
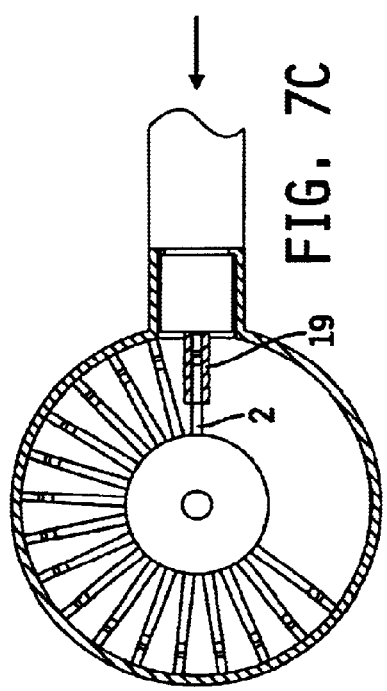

In FIG. 7 six partial FIGS. (A to F) show—like FIG. 3 and FIG. 5—how a lancing device (15) can be used to remove lancets (2) from the particularly preferred lancet magazine (1) of FIG. 6:

After the protecting cap (18) has been removed from the lancing device (15), the tip (17) with the guide groove (30) and the lancet holder (19) of the lancing device (15) are exposed (FIG. 7A). The lancing device (15) can now be inserted into the opening (9) of the socket (37) of the lancet magazine (1). In this process the guide groove (30) in the tip (17) of the lancing device (15) interacting with the guide pin (29) in the opening (9) of the lancet magazine (1) ensures an unequivocal orientation of the lancing device (15) relative to the lancet magazine (1). As soon as the tip (17) of the lancing device (15) has been completely inserted into the lancet magazine (1), the lancet (2) which is in the removal position is gripped by the lancet holder (19) (FIGS. 7B and C). Rotation of the lancing device (15) which is effected by the contour of the guide groove (30), rotates the lancet (2) together with the lancing device (15) around its longitudinal axis. In this process the point of the metal needle (11) is turned in the plastic disk (36) and is thus detached (FIG. 7D). When the lancing device (15) is removed from the lancet magazine (1), the lancet (2) is held by the lancet holder (19) in the lancing device (15) (FIG. 7E). The point of the metal (11) as well as the point of the metal needle (11) on the nearest part of the lancet body (12) protrude in this particularly preferred embodiment from the lancet holder (19) of the lancing device (15), the protecting cap must again by pushed over the tip (17) with the lancet holder, (19) of the lancing device (15) and turned relative to the grip body (16).

What is claimed is:

1. A system that is suitable for collecting bodily fluid from a region of the body of a person to be examined, the system comprising:
    a lancing device which is suitable for holding a lancet, the lancet including a needle;
    a lancet magazine for storing a plurality of lancets, the lancet magazine comprising an opening into which the landing device can be inserted to remove an individual lancet from the lancet magazine in a first direction substantially parallel to a longitudinal axis of the lancing device; and
    a transport device adapted to travel within the lancet magazine in a second direction substantially perpendicular to the first direction to transport lancets in the lancet magazine;
    wherein a second opening through which protective sheaths of the lancets can be ejected is located in the lancet magazine in addition to the opening into which the lancing device can be inserted to remove a single lancet from the lancet magazine.

2. A system that is suitable for collecting bodily fluid from a region of the body of a person to be examined, the system comprising:
    a lancing device which is suitable for holding a lancet, the lancet including a needle;
    a lancet magazine for storing a plurality of lancets, the lancet magazine comprising an opening into which the lancing device can be inserted to remove an individual lancet from the lancet magazine in a first direction substantially parallel to a longitudinal axis of the lancing device; and
    a transport device adapted to travel within the lancet magazine in a second direction substantially perpendicular to the first direction to transport lancets in the lancet magazine;
    wherein a pin is located in the opening of the lancet magazine into which the lancing device can be inserted to remove a single lancet from the lancet magazine, and the pin engages in a guide groove in the tip of the lancing device which is inserted into said opening and thus causes a rotation of the lancing device or a part of the lancing device about its longitudinal axis.

3. A system that is suitable for collecting bodily fluid from a region of the body of a person to-be examined, the system comprising:
    a lancing-device which is suitable for holding a lancet, the lancet including a needle;
    a lancet magazine for storing a plurality of lancets, the lancet magazine comprising an opening into which the lancing device can be inserted to remove an individual lancet from the lancet magazine in a first direction substantially parallel to a longitudinal axis of the lancing device; and
    a transport device adapted to travel within the lancet magazine in a second direction substantially perpendicular to the first direction to transport lancets in the lancet magazine;
    wherein a guide groove is located in the opening of the lancet magazine into which the lancing device can be inserted to remove a single lancet from the lancet magazine, and a pin is located in the tip of the lancing device which is inserted into said opening so that the pin engages the guide groove and thus causes a rotation of the lancing device or a part of the lancing device about its longitudinal axis.

4. A system that is suitable for collecting bodily fluid from a region of the body of a person to be examined, the system comprising:
    a lancing device which is suitable for holding a lancet, the lancet including a needle;
    a lancet magazine for storing a plurality of lancets, the lancet magazine comprising an opening into which the lancing device can be inserted to remove an individual lancet from the lancet magazine in a first direction substantially parallel to a longitudinal axis of the lancing device; and
    a transport device adapted to travel within the lancet magazine in a second direction substantially perpendicular to the first direction to transport lancets in the lancet magazine;

wherein the plurality of lancets in the lancet magazine each include a sterile tip and a protective sheath surrounding the sterile tip.

5. The system of claim 4, wherein the protective sheath is removed when the lancing device is inserted into the lancet magazine.

6. A system that is suitable for collecting bodily fluid from a region of the body of a person to be examined, the system comprising:

a lancing device which is suitable for holding a lancet, the lancet including a needle;

a lancet magazine for storing a plurality of lancets, the lancet magazine comprising an opening into which the lancing device can be inserted to remove an individual lancet from the lancet magazine in a first direction substantially parallel to a longitudinal axis of the lancing device; and a transport device adapted to travel within the lancet magazine in a second direction substantially perpendicular to the first direction to transport lancets in the lancet magazine;

wherein the opening has a substantially circular shape.

\* \* \* \* \*